(12) United States Patent
Trippel et al.

(10) Patent No.: US 6,604,050 B2
(45) Date of Patent: Aug. 5, 2003

(54) SYSTEM, METHOD AND BIOSENSOR APPARATUS FOR DATA COMMUNICATIONS WITH A PERSONAL DATA ASSISTANT

(75) Inventors: Christine G. Trippel, Mishawaka, IN (US); Robert D. Schell, Goshen, IN (US); Randall W. Miller, Goshen, IN (US); Joseph E. Perry, Osceola, IN (US); Starke S. Moore, Elkhart, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/865,522

(22) Filed: May 29, 2001

(65) Prior Publication Data

US 2001/0056328 A1 Dec. 27, 2001

Related U.S. Application Data

(60) Provisional application No. 60/211,964, filed on Jun. 16, 2000.

(51) Int. Cl.⁷ .............................................. G01N 33/48
(52) U.S. Cl. ..................... 702/19; 702/116; 702/121; 702/122; 702/130; 702/131
(58) Field of Search ........................ 702/19, 116, 121, 702/122, 130, 131; 323/911

(56) References Cited

U.S. PATENT DOCUMENTS

| | | | |
|---|---|---|---|
| 5,258,906 A | * | 11/1993 | Kroll et al. ............ 379/106.02 |
| 5,279,294 A | * | 1/1994 | Anderson et al. ........... 600/322 |
| 5,528,248 A | * | 6/1996 | Steiner et al. ......... 342/357.06 |
| 6,391,645 B1 | | 5/2002 | Huang et al. |

OTHER PUBLICATIONS

WO 01/52727 A1 publication date Jul. 26, 2001 by Minimed Inc., listed priority date of Jan. 20, 2000 and entitled "Handheld Personal Data Assistant (PDA) with a Medical Device and Method of Using the Same".

Published Pub. No.: US 2002/0002326 A1, Pub. Date Jan. 3, 2002, US patent application No. 09/935,827 filed Aug. 23, 2001, Continuation of application No. 09/487,423 filed Jan. 20, 2000 and entitled "Handheld Personal Data Assistant (PDA) with a Medical Device and Method of Using the Same".

* cited by examiner

Primary Examiner—John Barlow
Assistant Examiner—Meagan S. Walling
(74) Attorney, Agent, or Firm—Jerome L. Jeffers

(57) ABSTRACT

A system, method and biosensor apparatus are provided for data communications with a personal data assistant. The biosensor apparatus includes a sensor for receiving a user sample to be measured and a microcontroller for performing a predefined test sequence for measuring a predefined parameter value. An interface logic block is coupled to the microcontroller for communicating the predefined parameter data value to the personal data assistant. The personal data assistant provides an operator interface, data management and analysis of biosensor results.

19 Claims, 16 Drawing Sheets

SYSTEM, METHOD AND BIOSENSOR APPARATUS FOR DATA COMMUNICATIONS WITH A PERSONAL DATA ASSISTANT

This application claims the benefit of Provisional Application No. 60/211,964, filed Jun. 16, 2000.

FIELD OF THE INVENTION

The present invention generally relates to a biosensor, and, more particularly, to a new and improved system, method and biosensor apparatus for data communications with a personal data assistant.

DESCRIPTION OF THE PRIOR ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets, insulin intake and events. While the remainder of the disclosure herein will be directed towards the determination of glucose, it is to be understood that the procedure and apparatus of this invention can be used with other diagnostic systems.

Diagnostic systems, such as, blood glucose systems include a biosensor apparatus used to calculate the actual glucose value based on a measured output, such as, current or color, and the known reactivity of the reagent sensing element used to perform the test. The test results typically are displayed to the user and stored in a memory in the biosensor apparatus.

One known personal data assistant is a Palm™ handheld personal data assistant. It is desirable to provide a mechanism to enable the use a personal data assistant with a biosensor apparatus to eliminate the need for a user to manually enter data or go through a hook-up process to download measurements from a separate blood glucose monitor. A need exists for an efficient and effective mechanism to enable a biosensor to communicate with a personal data assistant. It is desirable to provide an improved method for storing and displaying information for use by a diabetic patient and also allows the user to augment stored glucose results by entering and storing insulin amounts and time as well as other relevant markers, for example, logbook capability.

SUMMARY OF THE INVENTION

An important object of the present invention is to provide a new and improved system, method and biosensor apparatus for data communications with a personal data assistant. Other important objects of the present invention are to provide such system, method and apparatus that eliminates or minimizes the need for user interaction; and to provide such method and apparatus substantially without negative effect; and that overcome some disadvantages of prior art arrangements.

In brief, a system, method and biosensor apparatus are provided for communications with a personal data assistant. The biosensor apparatus includes a sensor for receiving a user sample to be measured and a microcontroller for performing a predefined test sequence for measuring a predefined parameter value. An interface logic block is coupled to the microcontroller for communicating with the personal data assistant. The personal data assistant includes an interface logic block for communicating with the biosensor apparatus. The personal data assistant provides an operator interface, data management and analysis of biosensor results.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1:
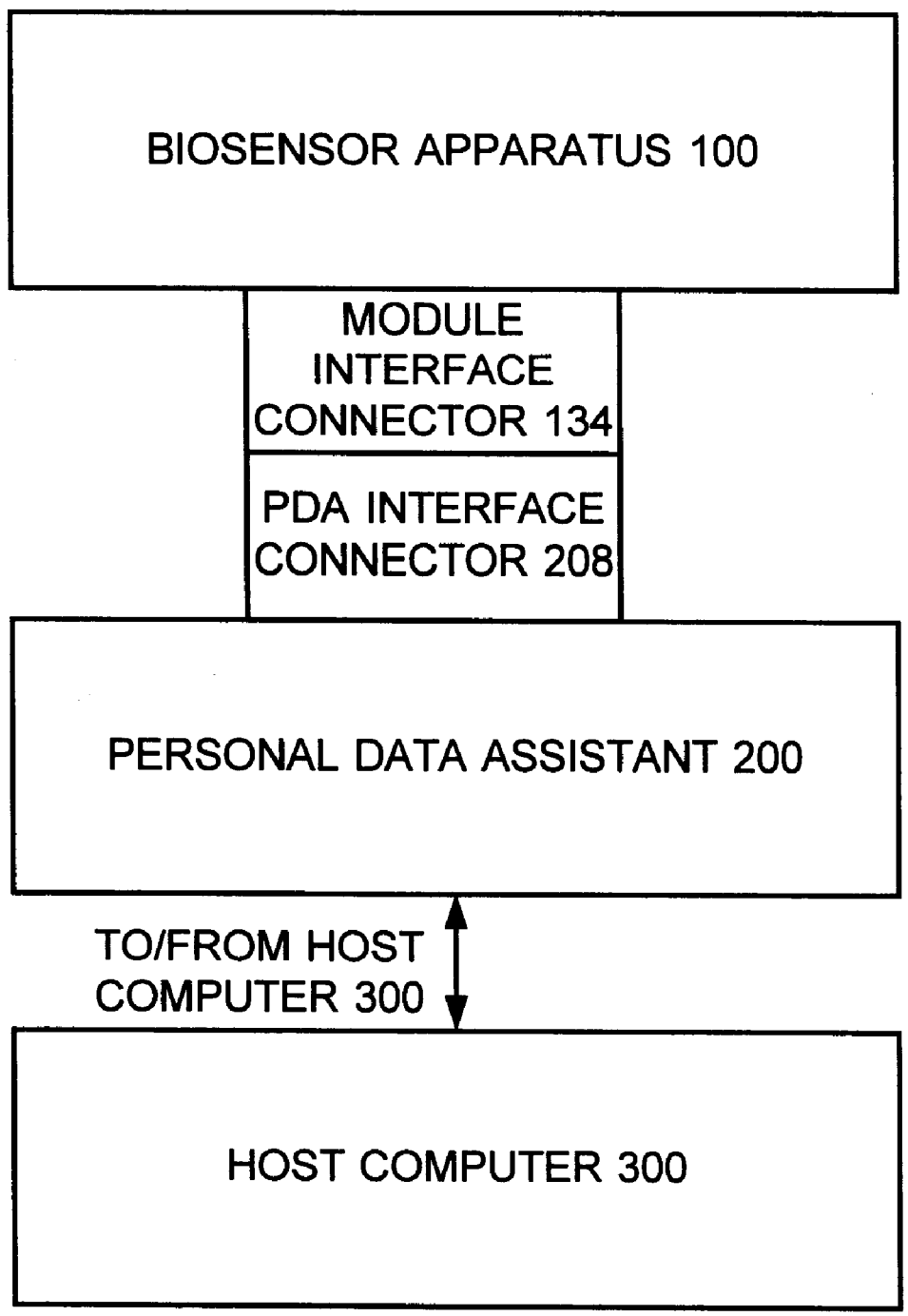
FIG. 1 is a block diagram representation of a system including a biosensor apparatus and a personal data assistant in accordance with the present invention.

Having reference now to the drawings, in FIG. 1 there is illustrated a system designated as a whole by the reference character 10 and arranged in accordance with principles of the present invention. System 10 includes a biosensor apparatus 100 used together with a personal data assistant 200. Personal data assistant 200 also is adapted for bi-directional communications with a host computer 300.

Figure 2:
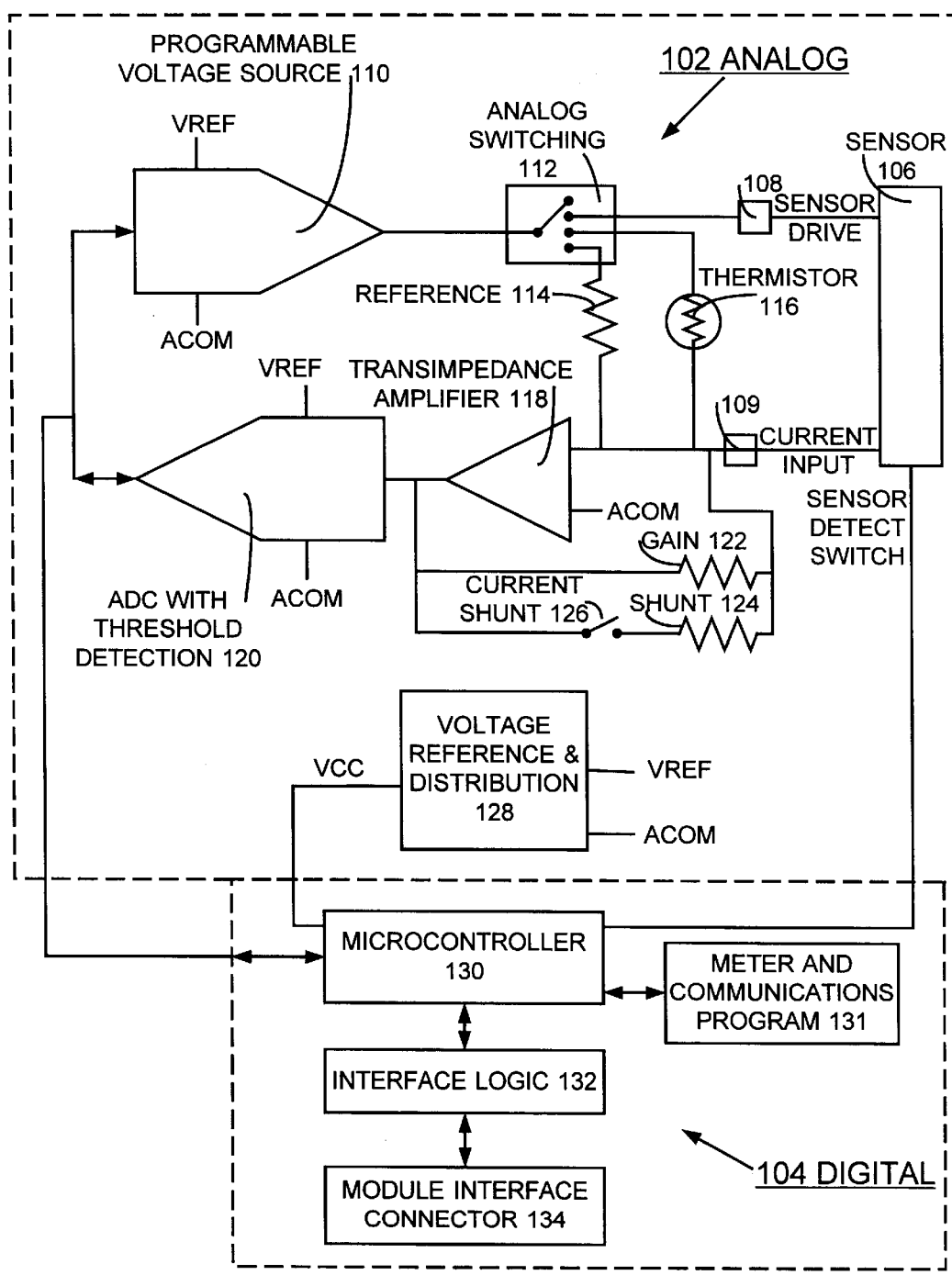
FIG. 2 is a block diagram representation of a biosensor apparatus in accordance with the present invention of the system of FIG. 1.

In FIG. 2 there is illustrated the biosensor apparatus designated as a whole by the reference character 100 and arranged in accordance with principles of the present invention. Biosensor apparatus 100 includes a data acquisition circuit generally designated by the reference character 102 and a microcontroller section generally designated by the reference character 104. Data acquisition circuit 102 includes a sensor 106 for receiving a blood sample from a user for performing a blood glucose test. A sensor drive input and a current input are applied to the sensor 106. One of a pair of electrostatic discharge suppressors 108 and 109 is coupled respectively to the sensor drive input and the current input. A programmable voltage source 110 is coupled to an analog switching device 112. A voltage reference VREF and an analog ground or common ACOM are applied to the programmable voltage source 110. Analog switching device 112 is also coupled to a reference resistor 114 and a thermistor 116. Both the reference resistor 114 and the thermistor 116 are also connected to a transimpedance amplifier 118. Analog switching device 112 couples a drive voltage or open to the sensor 106 at the sensor drive input.

The transimpedance amplifier 118 coupled to the sensor current input applies an input to an analog-to-digital converter (ADC) with threshold detection 120. A voltage reference VREF and an analog ground or common ACOM are applied to the ADC with threshold detection 120. A gain resistor 122 and a parallel, series connected shunt 124 and current shunt 126 are connected across the transimpedance amplifier 118. Data acquisition circuit 102 includes a voltage reference and distribution block 128 to supply reference voltages to the rest of the system. The sensor detect input connects to the microcontroller 130.

Microcontroller section 104 includes a microcontroller 130 receiving a voltage supply VCC input from the voltage reference and distribution block 128. A meter and communications program 131 is used with the microcontroller 130 in accordance with features of the preferred embodiment. Microcontroller is coupled to the programmable voltage source 110 and the ADC with threshold detection 120. Microcontroller section 104 includes an interface logic block 132 coupled between the microcontroller 130 and a module interface connector 134 enabling communications with the personal data assistant 200 of FIG. 2. Microcontroller 130 contains suitable programming to perform the methods of the invention as illustrated in FIGS. 5 and 14–16.

Figure 3:
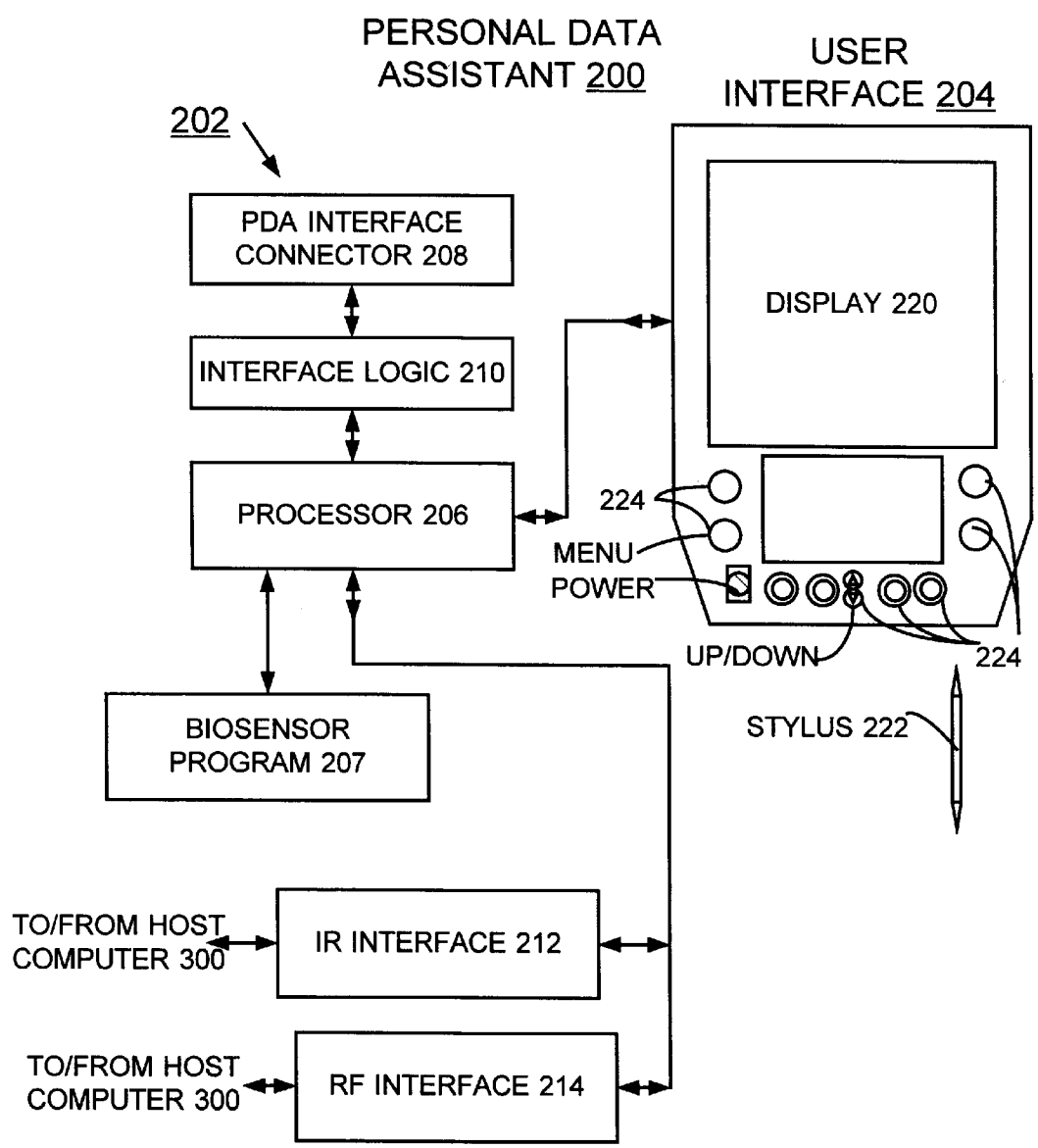
FIG. 3 is a block diagram representation of a personal data assistant used with the biosensor apparatus of FIGS. 1 and 2 in accordance with the present invention.

Referring to FIG. 3, the personal data assistant (PDA) 200 includes a processor section 202 and a user interface 204. The processor section 202 includes a processor 206 together with a biosensor program 207 in accordance with features of the preferred embodiment. Processor section 202 contains suitable programming to perform the methods of the invention as illustrated in FIGS. 4 and 6–13. The processor section 202 includes a PDA interface connector 208 enabling communications with the biosensor apparatus 100. An interface logic block 210 is coupled between the PDA interface connector 208 and the processor 206. An IR interface 212 and a RF interface 214 are coupled to the processor 206 for communications with a host computer 300. It should be understood that the principles of the present invention are not limited to the use of connectors 134 and 208 of FIGS. 2 and 3. For example, the IR interface 212 could be used with an IR port (not shown) on the biosensor apparatus 100 for communications between the biosensor apparatus 100 and the PDA 200.

PDA user interface 204 includes a touch sensitive display 220 coupled to the processor 206. PDA user interface 204 includes a stylus 222 for providing user selections. PDA user interface 204 includes a plurality of switches or buttons 224 for providing user selections.

In accordance with the invention, the desired system behavior includes that the user attaches the biosensor apparatus 100 to the PDA 200; the users inserts a strip into the biosensor apparatus 100; the PDA 200 turns on if it is off; or if it is on immediately runs the biosensor program. Then the biosensor apparatus 100 and meter and communications program 131, and PDA 200 and biosensor program 207, run in test mode.

To enable the biosensor apparatus 100 to wake up the PDA 200 when a strip is inserted, an interrupt line of PDA 200 is used. The PDA Modem Hotsync program also uses this interrupt line. Therefore the PDA Modem Hotsync button is re-mapped to run the biosensor program 207 and not the Modem Hotsync program. This re-mapping is done by setting the modem hotsync button in the Preferences program, a PDA supplied application. This re-mapping is performed at installation time. The default mapping of the hotsync modem button is to run the Modem Hotsync program.

In order to allow a user to hotsync their PDA 200 with a modem and then to use the biosensor program 207 a check in the biosensor communciations program is performed to see if the test module biosensor apparatus 100 is attached to the PDA 200 or a modem is attached to the PDA 200. When the biosensor program 207 starts up by the insertion of a test sensor strip, a check is done to see if the biosensor apparatus 100 is attached. If the biosensor apparatus 100 is attached then the biosensor communications program continues in Test mode. If the biosensor apparatus 100 is not attached then the biosensor program 207 terminates and the Modem Hotsync program is initiated.

After installation of the biosensor program 207, if the user modifies the mapping of the modem hotsync button (by the Preferences program) or a hard reset is done on the PDA 200 (which puts the modem hotsync button back to its default) the biosensor program 207 will not run when a user inserts a strip into the test module attached to the PDA 200. The logbook portion of the biosensor program 207 will still run because this program is started when the user taps on a predefined icon. The logbook portion is not started via the interrupt line.

If the user repeatedly inserts and removes a sensor without applying sample, the system will handle these multiple inserts thereby preventing the program from running multiple times.

Figure 4:
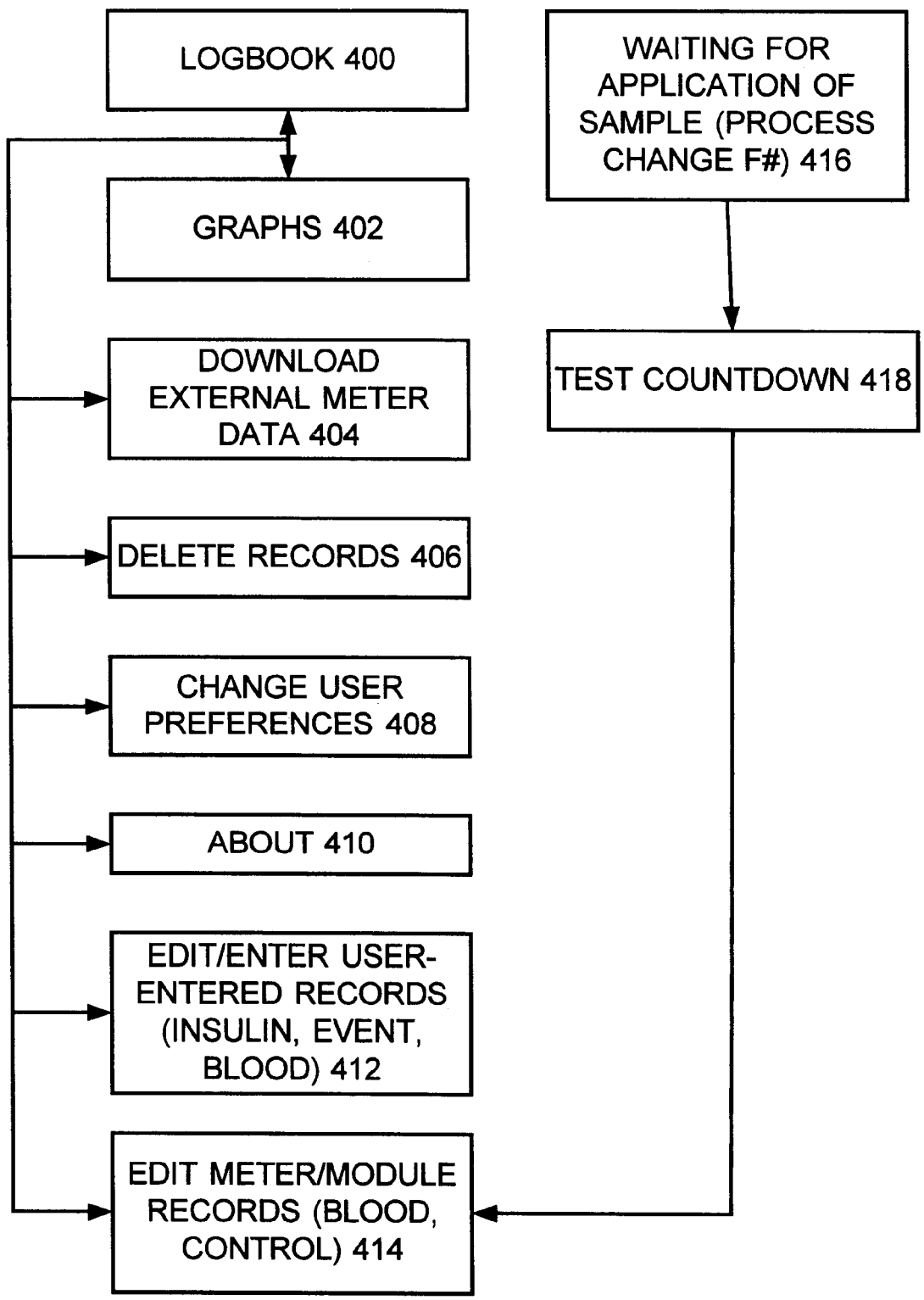
FIG. 4 is a flow chart illustrating exemplary user interface operations of the personal data assistant of FIG. 3 in the system of FIG. 1 in accordance with the present invention.

FIG. 4 illustrate exemplary user interface operations of system 10 including the biosensor apparatus 100 of FIG. 1 and the personal data assistant 200 of FIG. 2 in accordance with the present invention. A logbook block 400 is provided for displaying historical data and a graphs block 402 enables analysis of results data and graphical display of the historical data. A download external meter data block 404 enables downloading of data stored in the biosensor apparatus 100. A delete records block 406 enables the user to delete data records. A change user preferences block 408 enables the user to enter and update user preferences. An about block 410 is provided for displaying system information to the user. An edit/enter user-entered records block 412 is provided for the user to enter and edit records, such as insulin, event, blood, and the like. An edit meter records block 414 is provided for the user to edit records, meter and module records, such as markers, and the like. A waiting for application of sample block 416 enables the user to process a change in a code F# for a test strip and start a test. A test countdown block 418 displays a countdown for the user after a sample is applied to the test strip in the biosensor apparatus 100.

Figure 5:
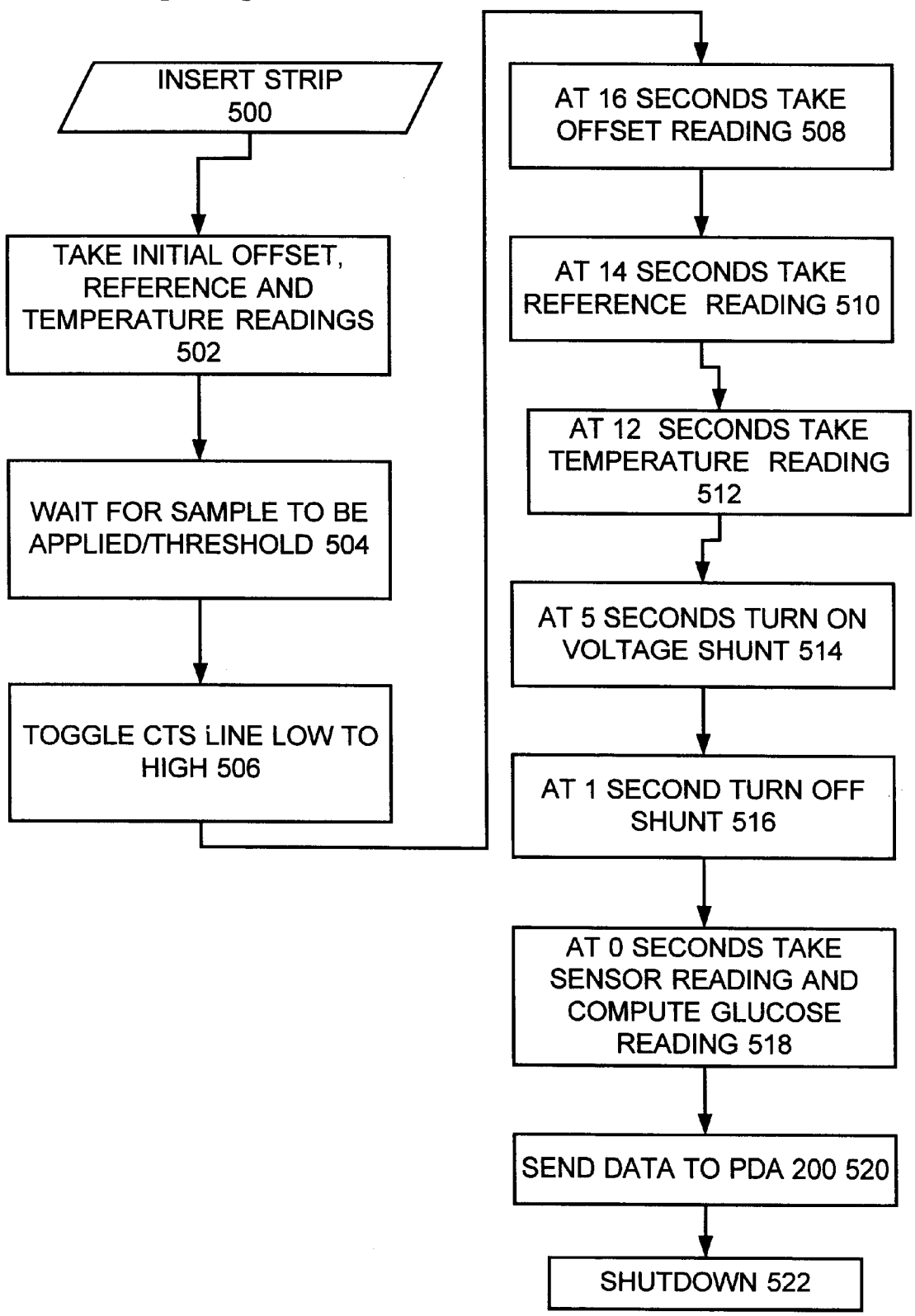
FIG. 5 is a flow chart illustrating exemplary sequential timing steps performed by the biosensor apparatus of FIGS. 1 and 2 in accordance with the present invention.

FIG. 5 illustrates exemplary sequential timing steps performed by the biosensor apparatus 100 in accordance with the present invention. In accordance with features of the invention, steps are taken to keep power usage to a minimum. When the serial port is enabled a charge pump in the PDA 200's RS232 interface chip uses a lot of power. To reduce power consumption the biosensor program 207 will briefly enable the serial port to monitor the clear to send (CTS) line. The CTS line is used to detect if the test module has been disconnected; to indicate when an error has occurred in the test module; to indicate when a sample has been applied to the test sensor; and to indicate a test complete.

In FIG. 5, a strip is inserted as indicated in a block 500. Initial offset, reference and temperature readings are taken as indicated in a block 502. Then waiting for a sample to be applied or threshold is performed as indicated in a block 504. Then the CTS line is toggled from low to high as indicated in a block 506. At a first set time, such as 16 seconds, an offset reading is taken as indicated in a block 508. At a second set time, such as 14 seconds, a reference reading is taken as indicated in a block 510. At a third set time, such as 12 seconds, a temperature reading is taken as indicated in a block 512. At a fourth set time, such as 5 seconds, the voltage shunt 124 in the biosensor apparatus 100 is turned on as indicated in a block 514. At a fifth set time, such as 1 second, the voltage shunt 124 in the biosensor apparatus 100 is turned off as indicated in a block 516. Finally, at 0 seconds, the sensor reading is takes and a glucose reading is computed as indicated in a block 518. The data is sent to the PDA 200 as indicated in a block 520. Then the biosensor apparatus 100 is shutdown as indicated in a block 522.

In accordance with features of the invention, steps are taken to maintain critical test timing. It is important to keep the user from wasting a strip. Because of the critical timing of the test countdown and the desire not to waste a strip, it is important to remain in the meter and communications program 131 while waiting for sample and during test countdown. Therefore external PDA 200 system interrupts are either ignored or delayed, for example, system timers, button presses, menu choices, or the power off button. Because the test timing is critical therefore the biosensor apparatus 100 handles all of the test timing and does not rely on the PDA 200. To conserve power the biosensor apparatus 100 is only turned on when a strip is inserted. The biosensor apparatus 100 generates an interrupt to wake up the PDA 200 so that the PDA 200 does not need to be running prior to the insertion of a strip. When a test has completed or when an error has occurred the biosensor apparatus 100 is shutdown immediately after reporting its status to the PDA 200. However, the PDA 200 will remain on. The system 10 has the capability of allowing the PDA 200 to wake up the biosensor apparatus 100 by asserting the data terminal ready (DTR) line. The communication protocol, as illustrated and described with respect to FIGS. 6–16, was designed to keep the power usage by both the PDA 200 and the biosensor apparatus 100 to a minimum.

Figure 6:
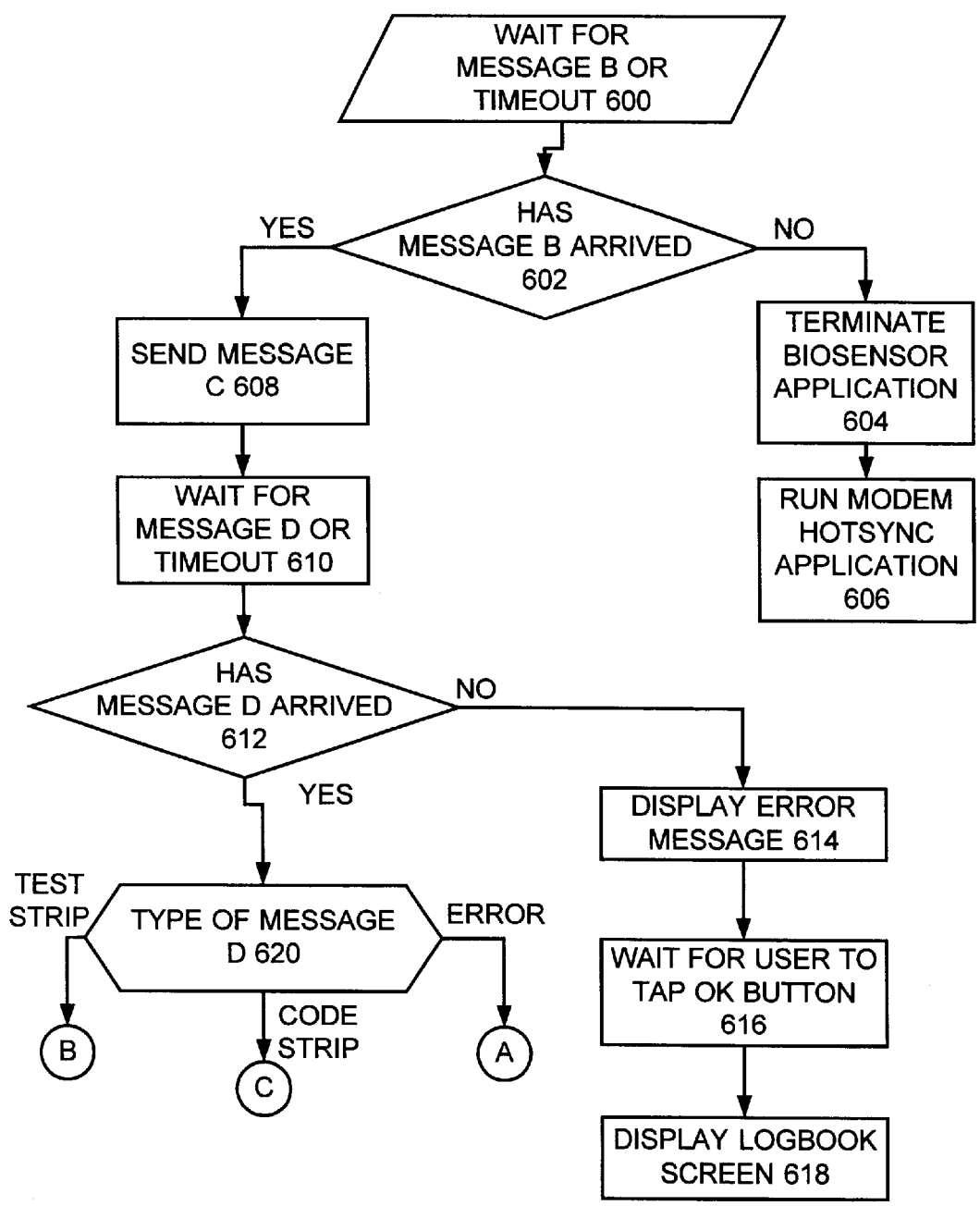
FIGS. 6–13 are flow charts illustrating exemplary sequential steps performed by the personal data assistant of FIGS. 1 and 3 in accordance with the present invention.

FIGS. 6–13 are flow charts illustrating exemplary sequential steps performed by the personal data assistant 200 in accordance with the present invention. Referring to FIG. 6, PDA 200 waits for a message B from the biosensor apparatus 100 or timeout as indicated in a block 600. The message B provides a software version number and reference method for the biosensor apparatus 100. Checking whether message B has arrived is performed as indicated in a decision block 602. If message B has not arrived, then the biosensor application is terminated as indicated in a block 604. Then the modem hotsync application is run as indicated in a block 606. When the message B has arrived, then a message C is sent to the biosensor apparatus 100 as indicated in a block 608. The message C is a query for a type of test strip. Next waiting for a message D from the biosensor apparatus 100 or a timeout is performed as indicated in a block 610. Checking whether message D has arrived is performed as indicated in a decision block 612. If message D has not arrived, then an error message is displayed as indicated in a block 614. Next waiting for the user to tap an OK button is performed as indicated in a block 616. Then the logbook screen is displayed as indicated in a block 618. If message D has arrived, then checking for a type of message D is performed as indicated in a block 620. With an error message, sequential operations continue following entry point A in FIG. 7. With a test strip message, sequential operations continue following entry point B in FIG. 7. With a code strip message, sequential operations continue following entry point C in FIG. 12.

Figure 7:
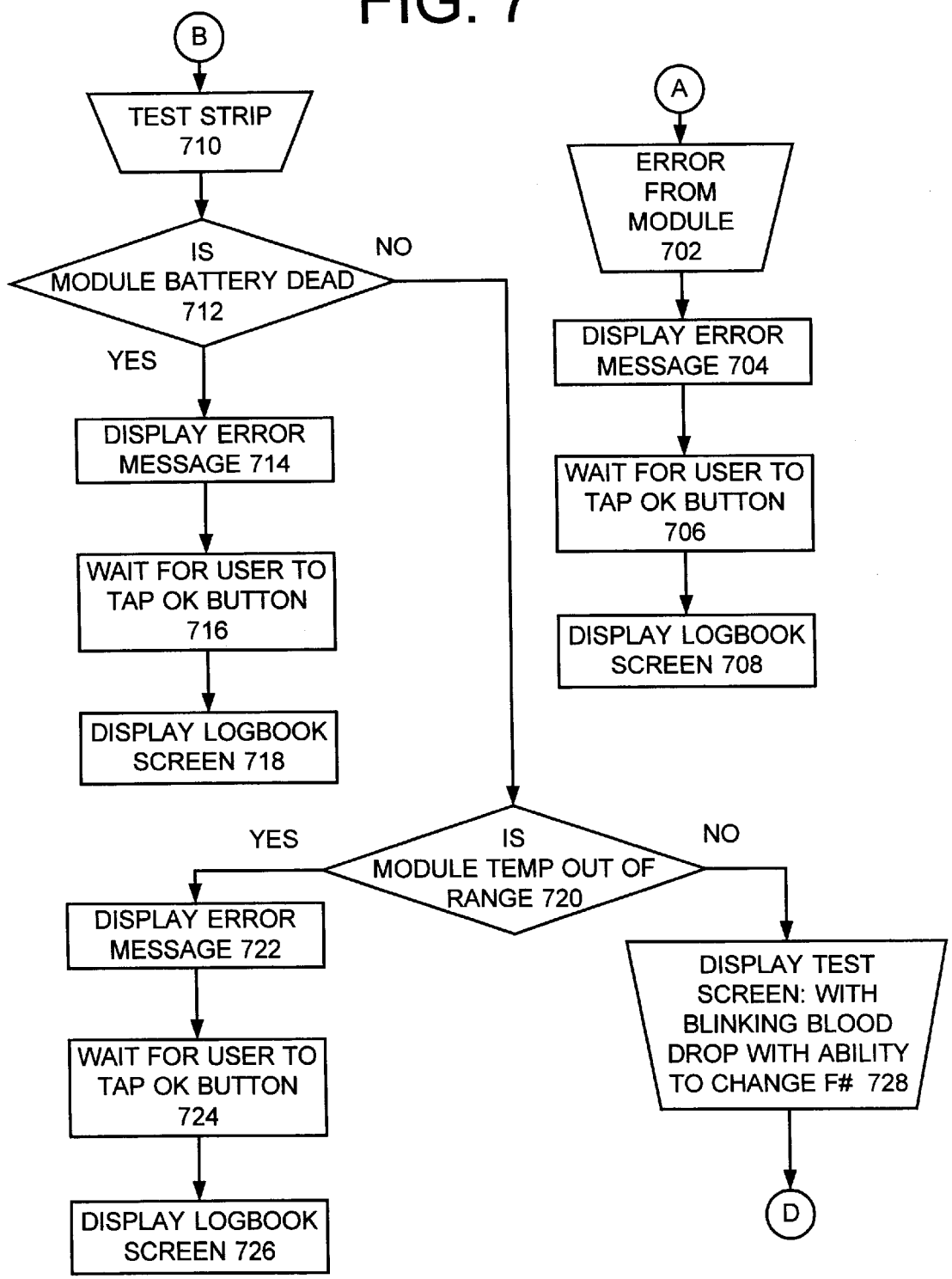

Referring to FIG. 7 following entry point A, an error from the module biosensor apparatus 100 is processed as indicated in a block 702. An error message is displayed as indicated in a block 704. Waiting for user to tap an OK button is performed as indicated in a block 706. Then the logbook screen is displayed as indicated in a block 708. Otherwise for a test strip message following entry point B, the test strip message is processed as indicated in a block 710. Checking whether the battery in the biosensor apparatus is dead is performed as indicated in a decision block 712. If the battery is dead, then an error message is displayed as indicated in a block 714. Waiting for user to tap an OK button is performed as indicated in a block 716. Then the logbook screen is displayed as indicated in a block 718. If the battery is not dead, then checking whether the temperature is out of range as indicated in a decision block 720. If the temperature is out of range, then an error message is displayed as indicated in a block 722. Waiting for user to tap an OK button is performed as indicated in a block 724. Then the logbook screen is displayed as indicated in a block 726. If the temperature is in range, then a test screen is displayed with a blinking blood drop and enabling the user to change the test strip code F# as indicated in a block 728. Then the sequential operations continue following entry point D in FIG. 8.

Figure 8:
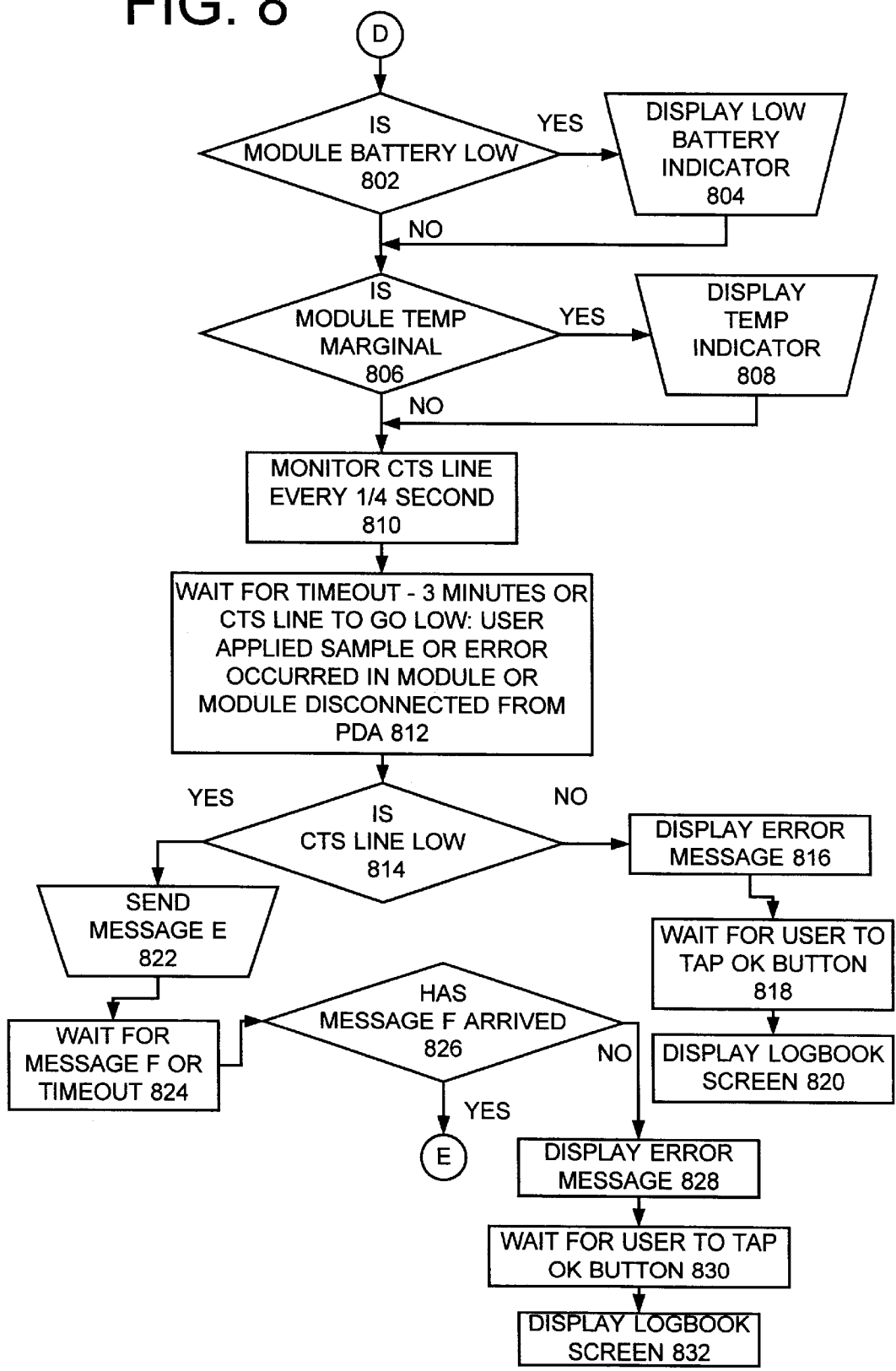

Referring to FIG. 8, following entry point D checking for a low battery status is performed as indicated in a decision block 802. If a low battery is identified, then a low battery indicator is displayed as indicated in a block 804. Next checking for a marginal temperature status is performed as indicated in a decision block 806. If a marginal temperature is identified, then a marginal temperature indicator is displayed as indicated in a block 808. Then the CTS line is monitored on a set time interval, such as every ¼ second as indicated in a block 810. Waiting for a timeout, such as 3 minutes or the CTS line to go low; with a user applied sample or an error for the module disconnected from the PDA as indicated in a block 812. Checking whether the CTS line is low is performed as indicated in a decision block 814. If the CTS line is not low, then an error message is displayed as indicated in a block 816. Waiting for user to tap an OK button is performed as indicated in a block 818. Then the logbook screen is displayed as indicated in a block 820. If the CTS line is low, then a message E is sent to query the biosensor apparatus whether the test has started as indicated in a block 822. Then waiting for a message F from the biosensor apparatus or a timeout is performed as indicated in a block 824. Checking whether message F has arrived is performed as indicated in a decision block 826. When the message F is not identified, then an error message is displayed as indicated in a block 828. Waiting for the user to tap OK button is performed as indicated in a block 830. Then the logbook screen is displayed as indicated in a block 832. When the message F is identified, then the sequential operations continue following entry point E in FIG. 9.

Figure 9:
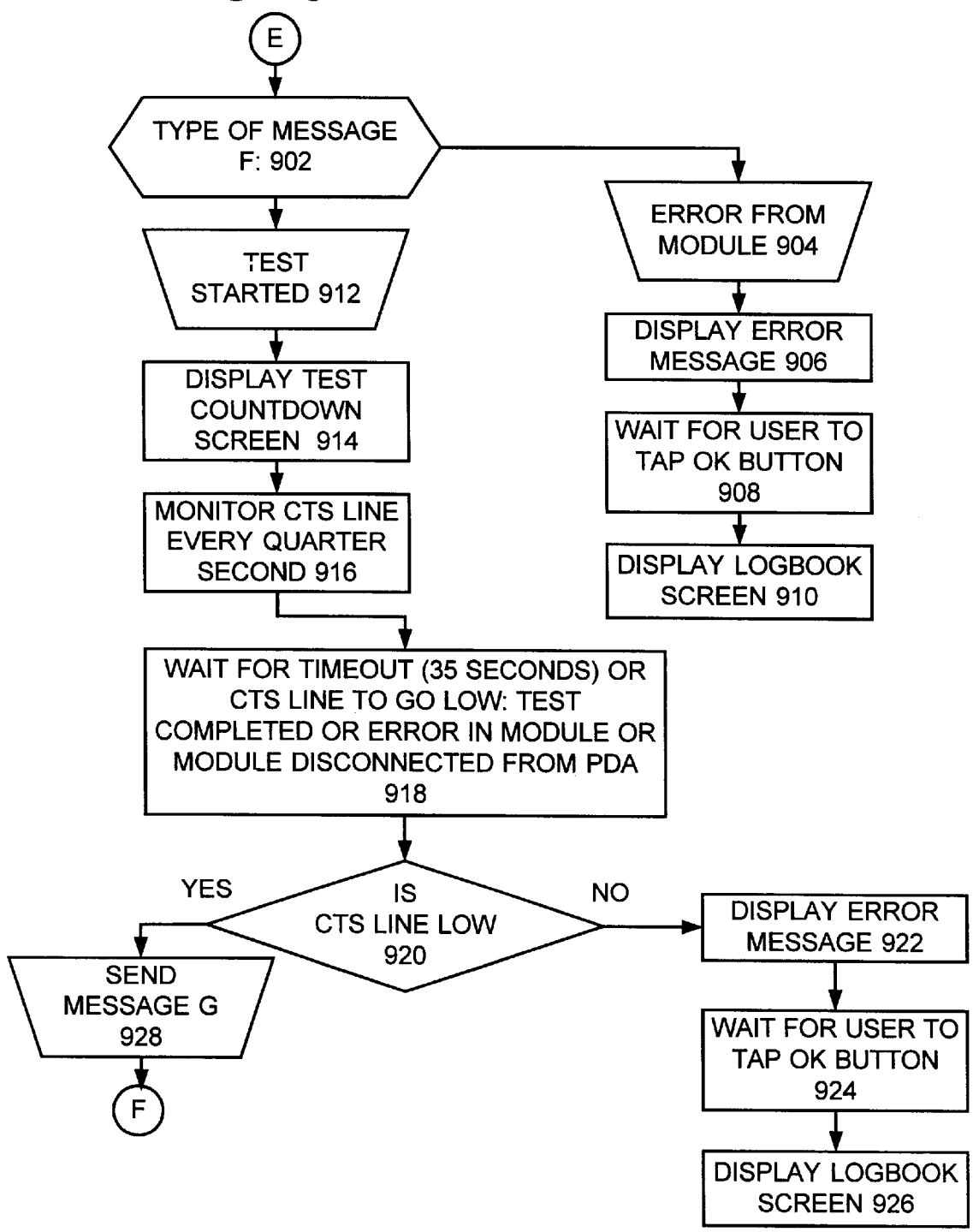

In FIG. 9, a type of message F is identified as indicated in a block 902. An error from the module is processed as indicated in a block 904. An error message is displayed as indicated in a block 906. Waiting for user to tap an OK button is performed as indicated in a block 908. Then the logbook screen is displayed as indicated in a block 910. Otherwise for a test started message is processed as indicated in a block 912. A test countdown screen is displayed as indicated in a block 914. The CTS line is monitored, for example every quarter second as indicated in a block 916.

Then waiting for a timeout, such as 35 seconds or the CTS line to go low for a completed test, an error in the module, or module disconnected from the PDA is performed as indicated in a block 918. Then checking whether the CTS line is low is performed as indicated in a decision block 920. If the CTS line is not low, then an error message is displayed as indicated in a block 922. Waiting for user to tap an OK button is performed as indicated in a block 924. Then the logbook screen is displayed as indicated in a block 926. If the CTS line is low, then a message G is sent as indicated in a block 928. Message G is a command and data message type for storing the F# (program #) in the biosensor apparatus. Sequential operations continue following entry point F in FIG. 10.

Figure 10:
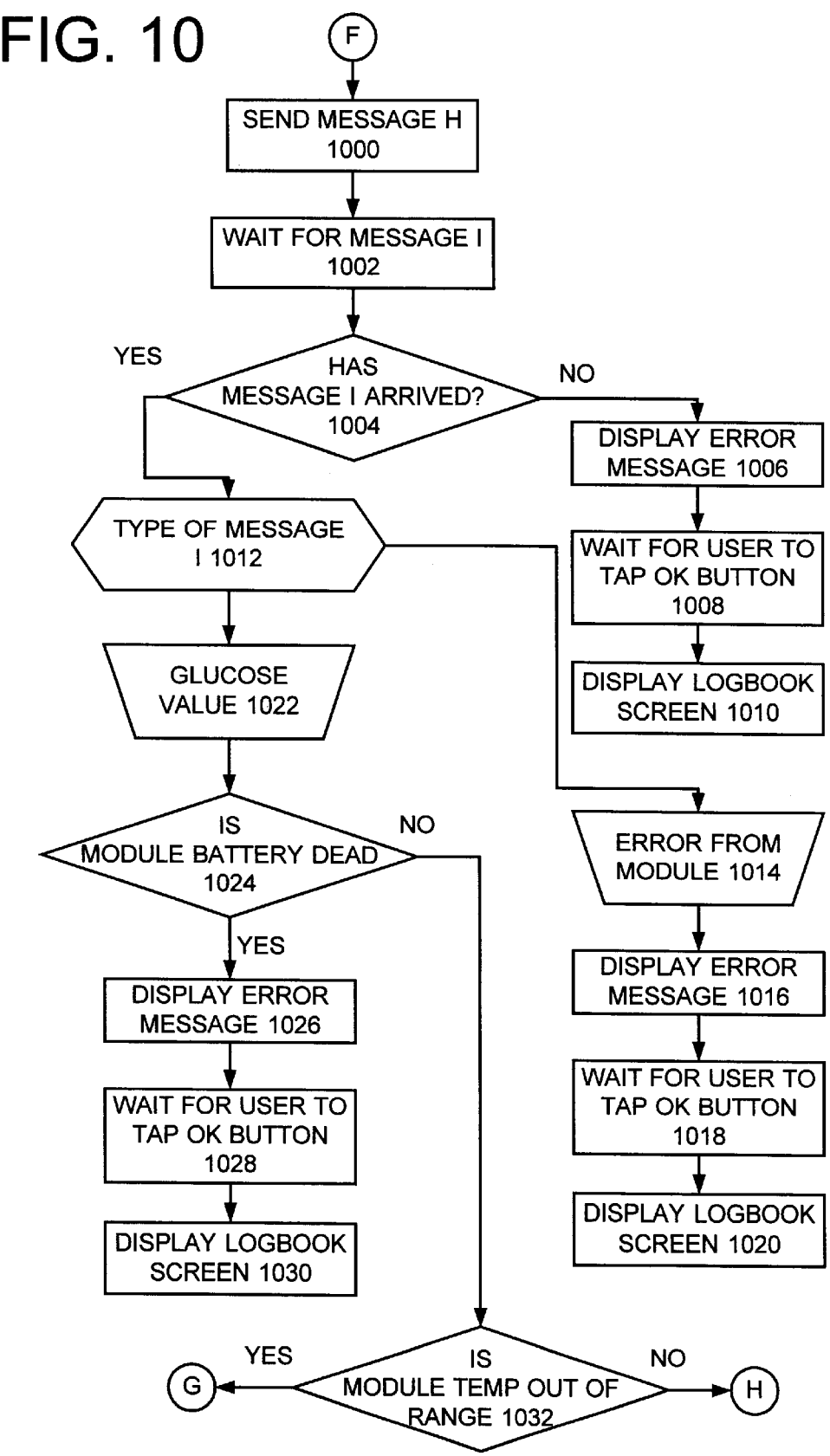

Referring to FIG. 10, next a message H is sent to query the module for the test value as indicated in a block 1000. Waiting for a message I response and the test value data is performed as indicated in a block 1002. Checking whether the message I has arrived is performed as indicated in a decision block 1004. When the message I has not arrived, then an error message is displayed as indicated in a block 1006. Waiting for user to tap an OK button is performed as indicated in a block 1008. Then the logbook screen is displayed as indicated in a block 1010. When the message I has arrived, then the type of message I is identified as indicated in a block 1012. An error from the module is processed as indicated in a block 1014. Then an error message is displayed as indicated in a block 1016. Waiting for user to tap an OK button is performed as indicated in a block 1018. Then the logbook screen is displayed as indicated in a block 1020. Otherwise, a glucose value is processed as indicated in a block 1022. Next checking whether the module battery is dead is performed as indicated in a block 1024. If the module battery is dead, then an error message is displayed as indicated in a block 1026. Waiting for user to tap an OK button is performed as indicated in a block 1028. Then the logbook screen is displayed as indicated in a block 1030. If the module battery is not dead, then checking whether the module temperature is out of range as indicated in a decision block 1032. If the module temperature is out of range, then sequential operations continue following entry point G in FIG. 11. If the module temperature is not out of range, then sequential operations continue following entry point H in FIG. 11.

Figure 11:
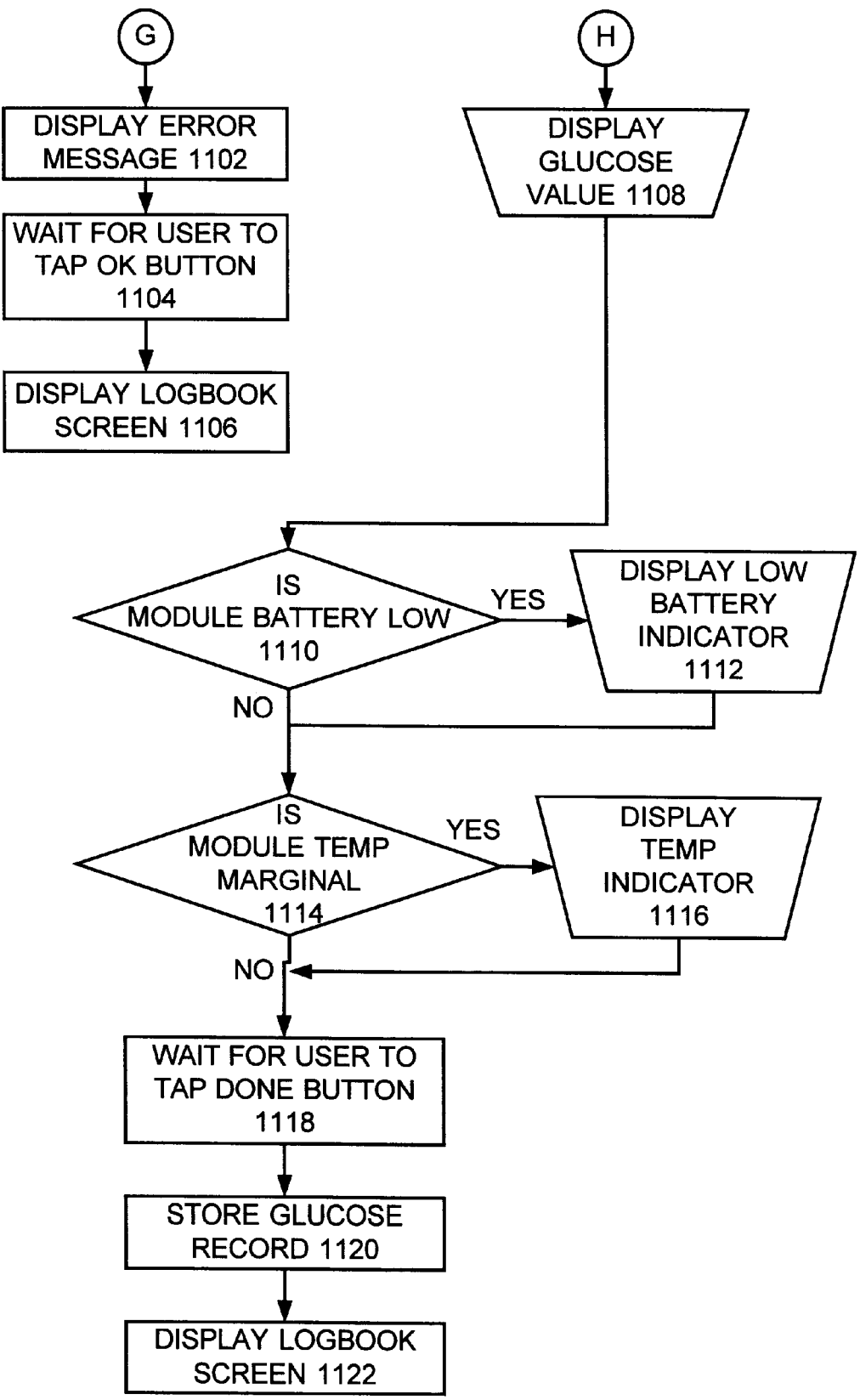

Referring to FIG. 11, following entry point G an error message is displayed as indicated in a block 1102. Waiting for user to tap an OK button is performed as indicated in a block 1104. Then the logbook screen is displayed as indicated in a block 1106. Following entry point H the glucose value is displayed as indicated in a block 1108. Checking for a low battery is performed as indicated in a decision block 1110. If a low battery is identified, then a low battery indicator is displayed as indicated in a block 1112. Checking for a marginal temperature is performed as indicated in a decision block 1114. If a marginal temperature is identified, then a marginal temperature indicator is displayed as indicated in a block 1116. Next waiting for the user to tap a DONE button is performed as indicated in a block 1118. The glucose record is stored as indicated in a block 1120. Then the logbook screen is displayed as indicated in a block 1122.

Figure 12:
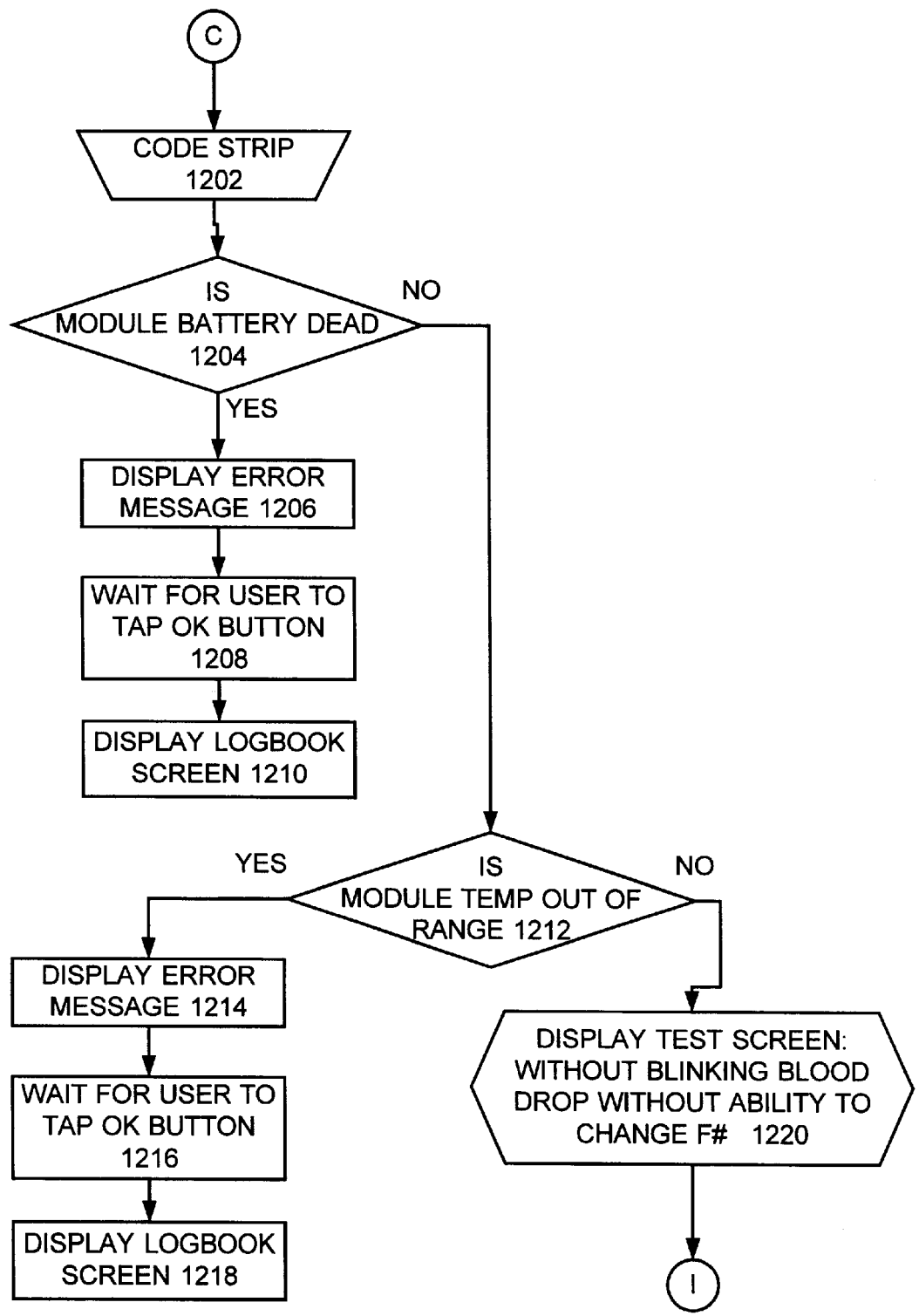

Referring to FIG. 12, following entry point C after a code strip message type is identified at block 620 in FIG. 6, the code strip message is processed as indicated in a block 1202. Checking whether the battery in the biosensor apparatus is dead is performed as indicated in a decision block 1204. If the battery is dead, then an error message is displayed as indicated in a block 1206. Waiting for user to tap an OK button is performed as indicated in a block 1208. Then the logbook screen is displayed as indicated in a block 1210. If the battery is not dead, then checking whether the temperature is out of range as indicated in a decision block 1212. If the temperature is out of range, then an error message is displayed as indicated in a block 1214. Waiting for user to tap an OK button is performed as indicated in a block 1216. Then the logbook screen is displayed as indicated in a block 1218. If the temperature is not out of range, then a test screen is displayed without the blinking blood drop and without enabling the user to change the test strip code F# as indicated in a block 1220. Then the sequential operations continue following entry point I in FIG. 13.

Figure 13:
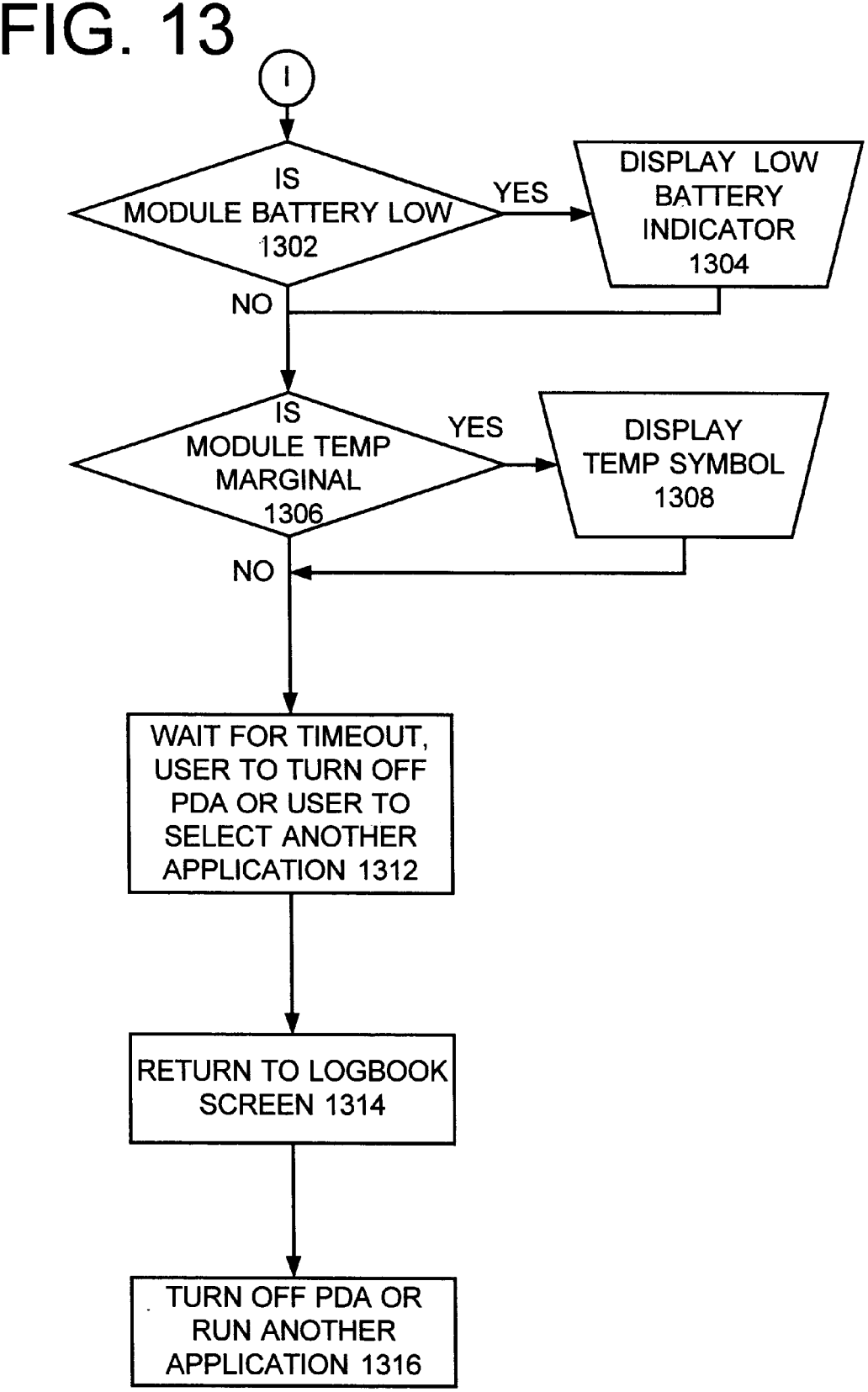

Referring to FIG. 13, following entry point I checking for a low battery status is performed as indicated in a decision block 1302. If a low battery is identified, then a low battery indicator is displayed as indicated in a block 1304. Next checking for a marginal temperature status is performed as indicated in a decision block 1306. If a marginal temperature is identified, then a marginal temperature indicator is displayed as indicated in a block 1308. Waiting for a timeout; the user to turn off the PDA; or the user to select another application is performed as indicated in a block 1312. Then the display returns to the logbook screen as indicated in a block 1314. Then the user turns off the PDA or runs another application as indicated in a block 1316.

Figure 14:
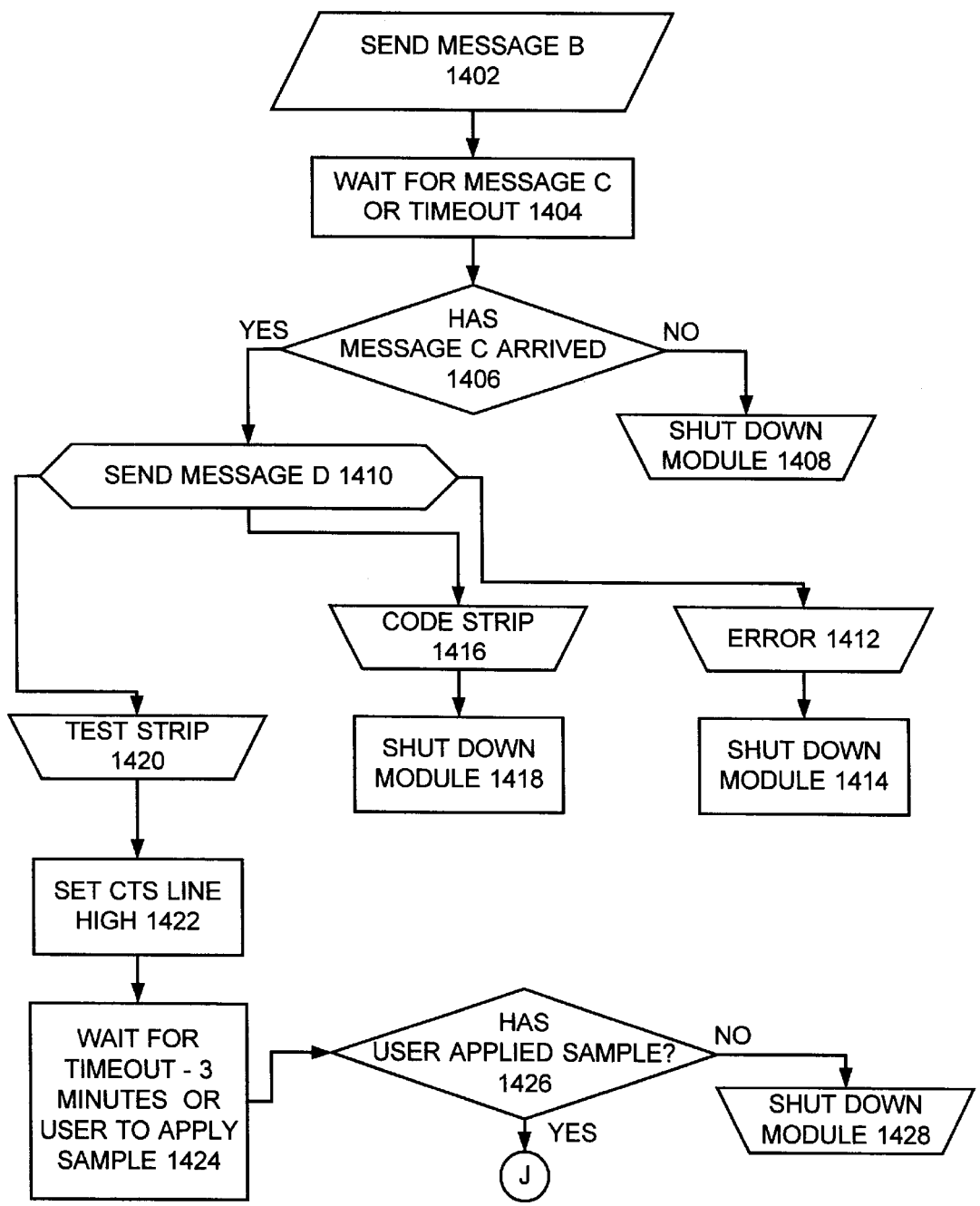
FIGS. 14–16 are flow charts illustrating exemplary sequential steps performed by the biosensor apparatus of FIGS. 1 and 2 in accordance with the present invention.
Figure 15:
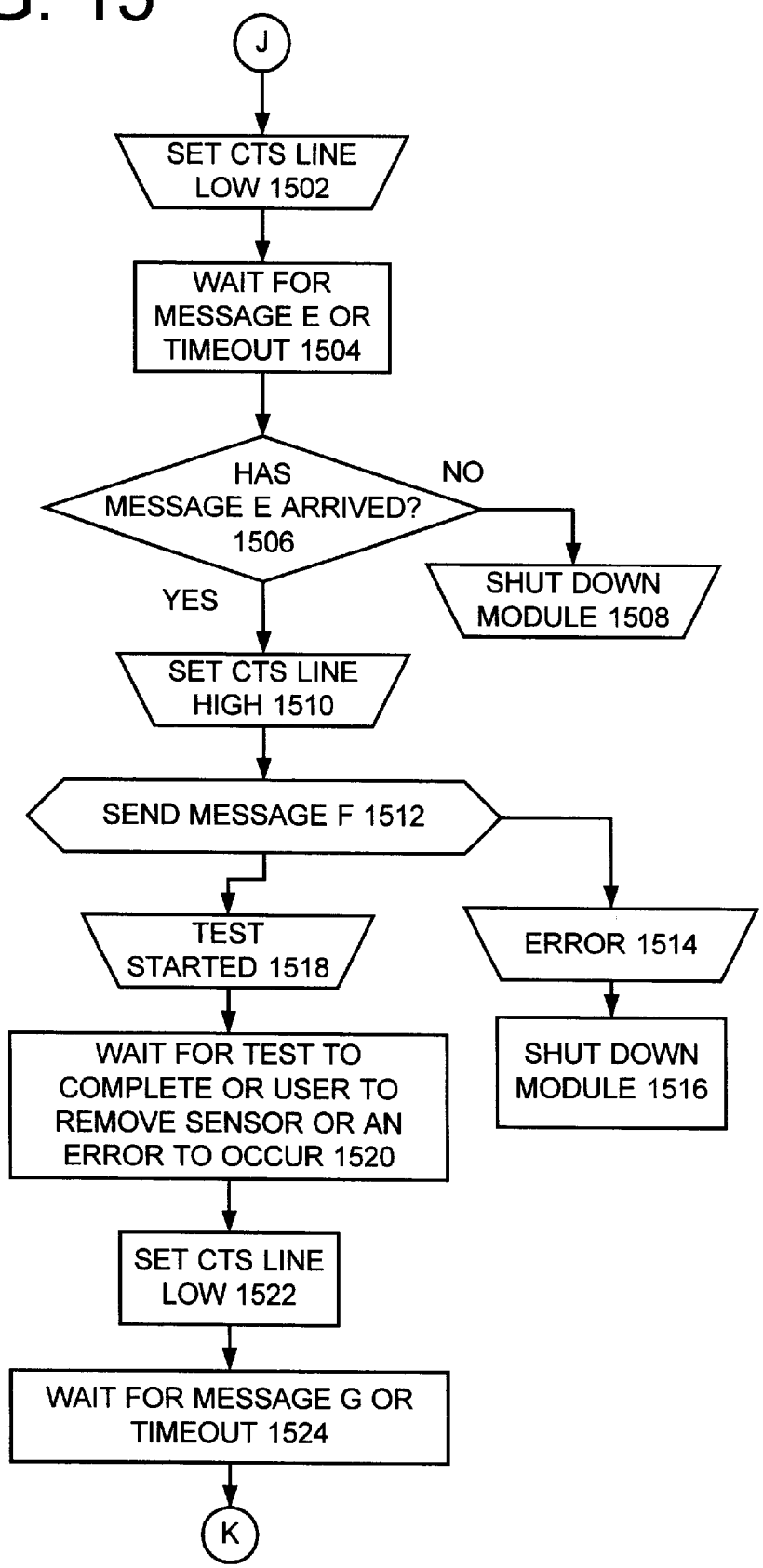
Figure 16:
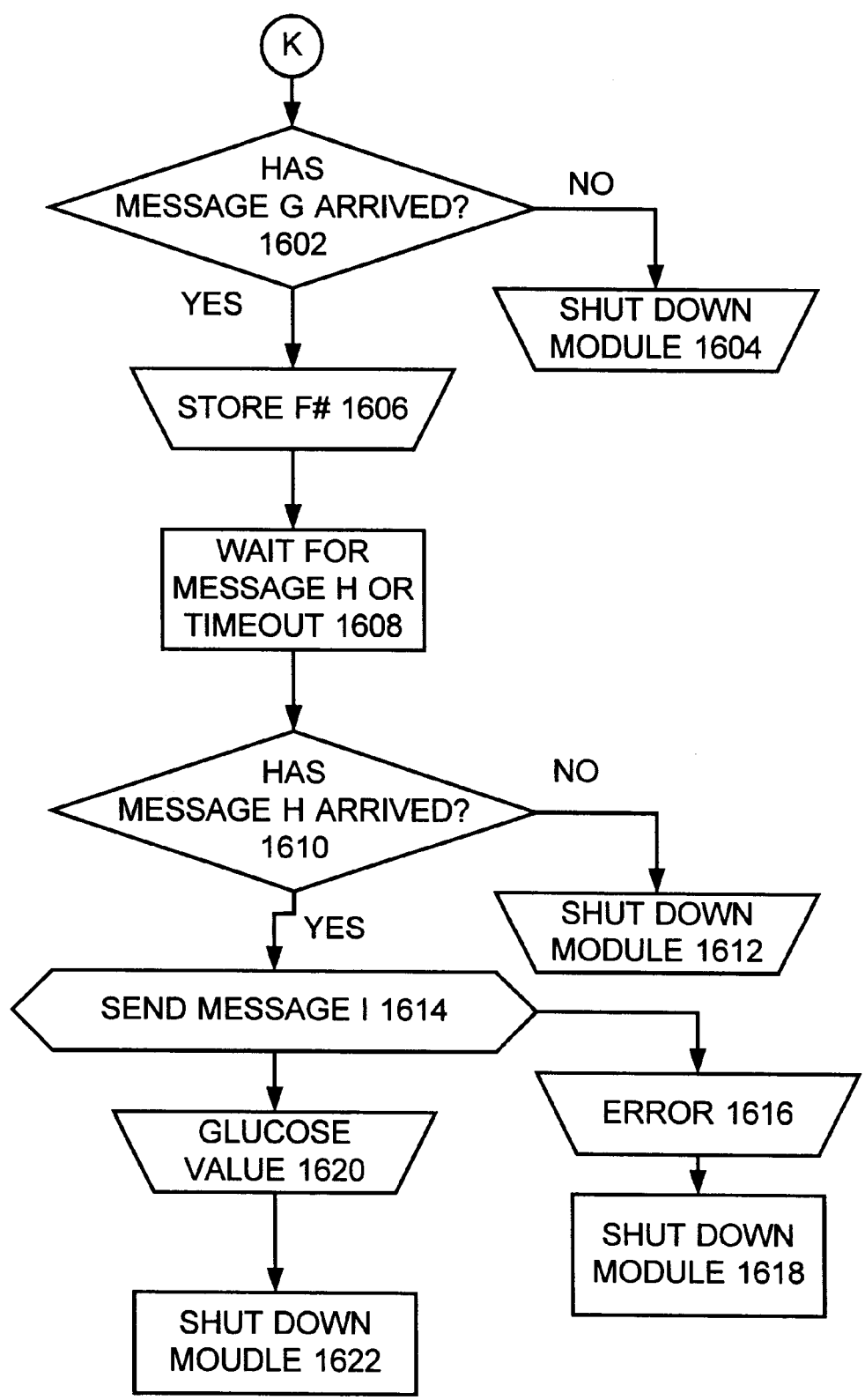

FIGS. 14–16 are flow charts illustrating exemplary sequential steps performed by the biosensor apparatus 100 in accordance with the present invention. Referring to FIG. 14, first the biosensor apparatus 100 sends a message B to the PDA as indicated in a block 1402. Message B provides a software version number. The biosensor apparatus 100 waits for the message C, query for type of test strip, from the PDA or a timeout as indicated in a block 1404. Checking whether message C has arrived is performed as indicated in a decision block 1406. When message C has not arrived, then the biosensor apparatus 100 is shut down as indicated in a block 1408. When message C has arrived, then the biosensor apparatus 100 sends message D as indicated in a block 1410. When an error and error code is sent as indicated in a block 1412, then the biosensor apparatus 100 is shut down as indicated in a block 1414. When a code strip response is sent as indicated in a block 1416, then the biosensor apparatus 100 is shut down as indicated in a block 1418. When a test strip response is sent as indicated in a block 1420, then the CTS line is set to high as indicated in a block 1422. Then the biosensor apparatus 100 waits for a timeout, such as after three minutes or for the user to apply a sample as indicated in a block 1424. Checking for a user applied sample is performed as indicated in a decision block 1426. When a user applied sample is not identified, then the biosensor apparatus 100 is shut down as indicated in a block 1428. When a user applied sample is identified, then the sequential operations continue following entry point J in FIG. 15.

Referring to FIG. 15, after a user applied sample is identified, then the CTS line is set low as indicated in a block 1502. Then the biosensor apparatus 100 waits for a message E or a timeout after a set number of seconds as indicated in a block 1504. Checking whether message E has arrived is performed as indicated in a decision block 1506. When message E has not arrived, then the biosensor apparatus 100 is shut down as indicated in a block 1508. When message E has arrived, then the biosensor apparatus 100 sets the CTS line high as indicated in a block 1510. The biosensor apparatus 100 sends a message F to the PDA as indicated in a block 1512. Message F provides an error as indicated in a block 1514. Then the biosensor apparatus 100 is shut down as indicated in a block 1516. Message F indicates that the test has started as indicated in a block 1518. Next the biosensor apparatus 100 waits for the test to complete, or the user to remove sensor or an error to occur as indicated in a block 1520. Then the biosensor apparatus 100 sets the CTS line low as indicated in a block 1522. Next the biosensor apparatus 100 waits for a message G or timeout as indicated in a block 1524. Then the sequential operations continue following entry point K in FIG. 16.

Referring to FIG. 16, checking whether message G has arrived is performed as indicated in a decision block 1602. When message G has not arrived, then the biosensor apparatus 100 is shut down as indicated in a block 1604. When message G has arrived, then the biosensor apparatus 100 stores the test strip code F# as indicated in a block 1606. Next the biosensor apparatus 100 waits for a message H from the PDA or a timeout as indicated in a block 1608. Message H is a query for the test value. Checking whether message H has arrived is performed as indicated in a decision block 1610. When message H has not arrived, then the biosensor apparatus 100 is shutdown as indicated in a block 1612. When message H has arrived, then the biosensor apparatus 100 sends a message I as indicated in a block 1614. Message I provides an error as indicated in a block 1616. Then the biosensor apparatus 100 is shut down as indicated in a block 1618. Message I indicates a glucose value as indicated in a block 1620. Then the biosensor apparatus 100 is shut down as indicated in a block 1622.

While the present invention has been described with reference to the details of the embodiments of the invention shown in the drawings, these details are not intended to limit the scope of the invention as claimed in the appended claims.

What is claimed is:

1. A system for communications between a biosensor apparatus and a personal data assistant, said system comprising:

the biosensor apparatus including
a sensor for receiving a user sample to be measured;
a microcontroller for performing a predefined test sequence for measuring a predefined parameter value;
an interface logic block coupled to said microcontroller for communicating with the personal data assistant;
the personal data assistant including an interface logic block for communicating with the biosensor apparatus; and the personal data assistant providing an operator interface, data management and analysis of biosensor results; the personal data assistant being activated for communicating with the biosensor apparatus during said predefined test sequence.

2. A system for communications between a biosensor apparatus and a personal data assistant, said system comprising:

the biosensor apparatus including
a sensor for receiving a user sample to be measured;
a microcontroller for a predefined test sequence for measuring a predefined parameter value;
an interface logic block coupled to said microcontroller for communicating with the personal data assistant;
the personal data assistant including an interface logic block for communicating with the biosensor apparatus; and the personal data assistant providing an operator interface, data management and analysis of biosensor results; the personal data assistant being activated for communicating with the biosensor apparatus during said predefined test sequence; and said microcontroller controlling timed measurements during said predefined test sequence for measuring said predefined parameter value.

3. A system for communications between a biosensor apparatus and a personal data assistant as recited in claim 2 wherein the personal data assistant displays predefined screens to the user for receiving user preferences and user entered records; for editing stored records; and for logbook functions; and for analysis and graphical display of biosensor results.

4. A system for communications between a biosensor apparatus and a personal data assistant, said system comprising:

the biosensor apparatus including
a sensor for receiving a user sample to be measured;
a microcontroller for performing a predefined test sequence for measuring a predefined parameter value;
an interface logic block coupled to said microcontroller for communicating with the personal data assistant;
the personal data assistant including an interface logic block for communicating with the biosensor apparatus; and the personal data assistant providing an operator interface, data management and analysis of biosensor results; the personal data assistant being activated for communicating with the biosensor apparatus during said predefined test sequence; and
wherein said microcontroller detects insertion of said sensor; said microcontroller applies an interrupt to the personal data assistant responsive to said sensor being inserted and said microcontroller sends predefined messages to the personal data assistant during said predefined test sequence.

5. A system for communications between a biosensor apparatus and a personal data assistant as recited in claim 4 wherein the personal data assistant displays a test screen enabling the user to change a test strip code; and the personal data assistant sends at least one predefined message to the biosensor apparatus during said predefined test sequence.

6. A system for communications between a biosensor apparatus and a personal data assistant, said system comprising:

the biosensor apparatus including
a sensor for receiving a user sample to be measured;
a microcontroller for performing a predefined test sequence for measuring a predefined parameter value;
an interface logic block coupled to said microcontroller for communicating with the personal data assistant;
the personal data assistant including an interface logic block for communicating with the biosensor apparatus; and the personal data assistant providing an operator interface, data management and analysis of biosensor results; the personal data assistant being activated for communicating with the biosensor apparatus during said predefined test sequence; and
wherein the personal data assistant monitors a clear to send (CTS) line; and said microcontroller uses said CTS line to indicate said sensor being inserted to start said predefined test sequence and said microcontroller uses said CTS line to indicate an applied sample to said sensor.

7. A system for communications between a biosensor apparatus and a personal data assistant as recited in claim 6 wherein said microcontroller sends a test started message to the personal data assistant to start said predefined test sequence.

8. A system for communications between a biosensor apparatus and a personal data assistant as recited in claim 7 wherein the personal data assistant displays a countdown screen responsive to said test started message; and the personal data assistant sends a predefined query message to the biosensor apparatus, said predefined query message for requesting a test result value.

9. A system for communications between a biosensor apparatus and a personal data assistant as recited in claim 8 wherein said microcontroller sends said test result value to the personal data assistant and the personal data assistant displays said test result value.

10. A method for implementing communications between a biosensor apparatus and a personal data assistant comprising the steps of:

provide the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant; and utilizing the personal data assistant for providing an operator interface, data management and analysis of biosensor results; and for communicating with the biosensor apparatus during said predefined test sequence.

11. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant;

utilizing the personal data assistant for providing an operator interface, data management and analysis of biosensor results; and for communicating with the biosensor apparatus during said predefined test sequence; and said microcontroller applying an interrupt to the personal data assistant responsive to said sensor being inserted.

12. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant;

utilizing the personal data assistant for providing an operator interface, data management and analysis of biosensor results; and for communicating with the biosensor apparatus during said predefined test sequence; and the personal data assistant monitoring a clear to send (CTS) line; and said microcontroller using said CTS line to indicate an applied sample to said sensor; a competed test and when an error has occurred.

13. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant;

utilizing the personal data assistant for providing an operator interface, data management and analysis of biosensor results; and for communicating with the biosensor apparatus during said predefined test sequence; and said microcontroller sending a predefined message identifying said inserted sensor and status of the biosensor apparatus to the personal data assistant; and the personal data assistant displaying a predefined test screen to prompt the user to apply a sample.

14. A method for implementing communications between a biosensor apparatus and a personal data assistant as recited in claim 13 wherein the personal data assistant monitors a clear to send (CTS) line to indicate an applied sample to said sensor.

15. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant;

utilizing the personal data assistant for providing an operator interface, data management and analysis of biosensor results; and for communicating with the biosensor apparatus during said predefined test sequence; and said microcontroller sending a predefined test started message to the personal data assistant to start said predefined test sequence.

16. A method for implementing communications between a biosensor apparatus and a personal data assistant as recited in claim 15 wherein the personal data assistant displays a countdown screen responsive to said predefined test started message.

17. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for activating the personal data assistant during said predefined test sequence; and for transferring status information and said predefined parameter value to the personal data assistant;

utilizing the personal data assistant for providing an operator interface, data management and analysis of biosensor results; and for communicating with the biosensor apparatus during said predefined test sequence; and said microcontroller sending a predefined test results message to the personal data assistant; and the personal data assistant displaying a test results screen responsive to said predefined test results message.

18. A method for implementing communications between a biosensor apparatus and a personal data assistant as recited in claim 17 wherein the biosensor apparatus shuts down responsive to sending said predefined test results message.

19. A method for implementing communications between a biosensor apparatus and a personal data assistant comprising the steps of:

providing the biosensor apparatus with a sensor for receiving a user sample and a microcontroller for performing a predefined test sequence for measuring a predefined parameter value;

utilizing the biosensor apparatus for transferring status information and said predefined parameter value to the personal data assistant;

utilizing the personal data assistant for providing an operator interface, data management and analysis of biosensor results; and responsive to the biosensor apparatus transferring an error status information, the personal data assistant displays an error message and then displays a logbook screen.

* * * * *